(12) United States Patent
Gavin et al.

(10) Patent No.: US 11,925,168 B2
(45) Date of Patent: Mar. 12, 2024

(54) MILKING SYSTEM WITH DETECTION SYSTEM

(71) Applicant: LELY PATENT N.V., Maassluis (NL)

(72) Inventors: Peter Michael Gavin, Maassluis (NL); Darby Anne McChesney, Maassluis (NL); Abram Christiaan Knip, Maassluis (NL)

(73) Assignee: LELY PATENT N.V., Maassluis (NL)

( * ) Notice: Subject to any disclaimer, the term of this patent is extended or adjusted under 35 U.S.C. 154(b) by 475 days.

(21) Appl. No.: 17/274,129

(22) PCT Filed: Sep. 19, 2019

(86) PCT No.: PCT/NL2019/050620
§ 371 (c)(1),
(2) Date: Mar. 5, 2021

(87) PCT Pub. No.: WO2020/067882
PCT Pub. Date: Apr. 2, 2020

(65) Prior Publication Data
US 2021/0195863 A1 Jul. 1, 2021

(30) Foreign Application Priority Data
Sep. 24, 2018 (NL) .................................... 2021691

(51) Int. Cl.
*A01J 5/013* (2006.01)
*A01J 5/003* (2006.01)
(Continued)

(52) U.S. Cl.
CPC ............... *A01J 5/007* (2013.01); *A01J 5/003* (2013.01); *A01J 5/0131* (2013.01);
(Continued)

(58) Field of Classification Search
CPC .......... A01J 5/007; A01J 5/003; A01J 5/0131; G01N 1/2035; G01N 21/8483;
(Continued)

(56) References Cited

U.S. PATENT DOCUMENTS 4,497,898 A * 2/1985 Anderson ............ G01N 21/534
422/74
4,959,976 A * 10/1990 Matsuda .......... G01N 35/00009
62/271

(Continued)

FOREIGN PATENT DOCUMENTS

| CN | 103228127 A | 7/2013 |
|---|---|---|
| CN | 104704383 A | 6/2015 |

(Continued)

OTHER PUBLICATIONS

Chinese Office Action and Search Report for Chinese Application No. 201980058666.3, dated Feb. 15, 2022, with English translation.

(Continued)

*Primary Examiner* — David J Bolduc
(74) *Attorney, Agent, or Firm* — Birch, Stewart, Kolasch & Birch, LLP

(57) ABSTRACT

A milking system includes a milking device with a milking control, a milk line, and a sampling/analysis device. The milking control controls the milking based on said analysis. The sampling/analysis device includes a reagent carrier, including a tape with a first side with a reagent pad that detects the presence of a substance in the milk sample and a second side, a dosing device to provide a droplet of said sample onto the reagent pad, a source for emitting source radiation onto the reagent pad, and a sensor to detect response radiation emitted by the reagent pad, and to analyse the detected response radiation to indicate the presence or concentration of said substance. The first side faces away from the sensor during analysing by the sensor. By viewing (Continued)

Figure 1:
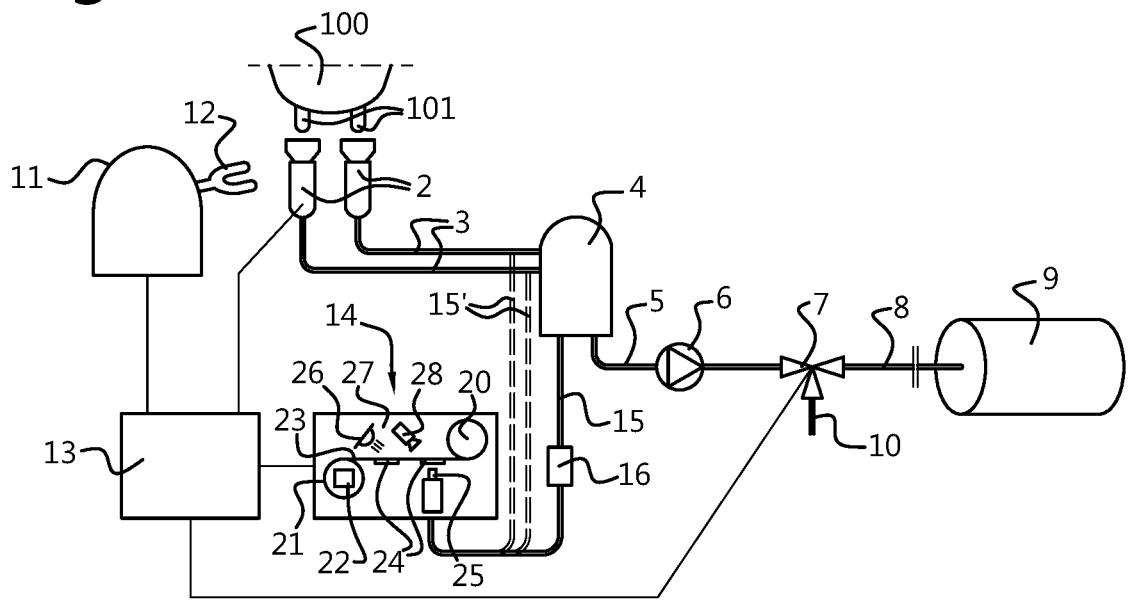

"from below", the observed reaction in the reagent is cleaner, and suffers less from artefacts, and the camera will stay cleaner.

16 Claims, 1 Drawing Sheet

(51) Int. Cl.
*A01J 5/007* (2006.01)
*G01N 1/20* (2006.01)
*G01N 21/84* (2006.01)
*G01N 33/04* (2006.01)

(52) U.S. Cl.
CPC ....... *G01N 1/2035* (2013.01); *G01N 21/8483* (2013.01); *G01N 33/04* (2013.01)

(58) Field of Classification Search
CPC .. G01N 33/04; G01N 1/10; G01N 2021/7773; G01N 2021/7786; G01N 35/00009
See application file for complete search history.

(56) References Cited

U.S. PATENT DOCUMENTS

| | | | |
|---|---|---|---|
| 5,096,828 A | | 3/1992 | Ishizaka et al. |
| 5,100,620 A | * | 3/1992 | Brenneman .......... G01N 1/2813 422/417 |
| 5,120,506 A | * | 6/1992 | Saito .......... B01L 1/02 422/66 |
| 5,139,743 A | * | 8/1992 | Ishizaka .......... G01N 35/00663 422/66 |
| 5,204,268 A | * | 4/1993 | Matsumoto ........ G01N 35/1009 422/66 |
| 5,743,209 A | * | 4/1998 | Bazin ........ A01J 5/007 119/14.08 |
| 5,837,546 A | * | 11/1998 | Allen ................ G01N 33/5438 422/403 |
| 6,731,100 B1 | * | 5/2004 | Hansen ................ G01N 21/59 324/637 |
| 2002/0124803 A1 | | 9/2002 | Chen et al. |
| 2005/0225766 A1 | * | 10/2005 | Hansen ............. G01N 15/1463 356/436 |
| 2006/0260939 A1 | | 11/2006 | Anderson et al. |
| 2008/0057596 A1 | * | 3/2008 | Law ........................ G01N 21/78 436/166 |
| 2008/0283537 A1 | | 11/2008 | Smith et al. |
| 2009/0304247 A1 | * | 12/2009 | Petrich ................ G01N 21/8483 382/128 |
| 2010/0047848 A1 | * | 2/2010 | Law ................... G01N 33/5005 435/29 |
| 2010/0311181 A1 | * | 12/2010 | Abraham ............. G01N 33/558 422/68.1 |
| 2010/0317094 A1 | * | 12/2010 | Ricco ..................... G01N 33/04 435/287.1 |
| 2012/0083044 A1 | * | 4/2012 | Sturman .............. G01N 33/689 422/402 |
| 2012/0125261 A1 | * | 5/2012 | Van Den Berg ......... A01K 1/12 119/14.02 |
| 2012/0138787 A1 | * | 6/2012 | Wilson ................ H01J 49/0027 250/288 |
| 2012/0179383 A1 | * | 7/2012 | Yeo ....................... G01N 21/278 73/1.01 |
| 2013/0177214 A1 | * | 7/2013 | Markovsky ............ G01N 33/04 382/110 |
| 2013/0203613 A1 | * | 8/2013 | Burmeister ....... B01L 3/502715 506/18 |
| 2014/0273271 A1 | * | 9/2014 | Aizawa ............ G01N 33/54373 422/429 |
| 2017/0173578 A1 | * | 6/2017 | Crooks .................. G01N 33/68 |
| 2021/0208122 A1 | * | 7/2021 | Vandevelde ........... G01N 27/06 |

FOREIGN PATENT DOCUMENTS

| | | |
|---|---|---|
| CN | 106455517 A | 2/2017 |
| EP | 0666475 A2 | 8/1995 |
| WO | WO 02/069697 A1 | 9/2002 |
| WO | WO 2004/034063 A2 | 4/2004 |
| WO | WO 2014/012558 A2 | 1/2014 |
| WO | WO 2014/012558 A3 | 1/2014 |
| WO | WO 2020/067876 A1 | 4/2020 |

OTHER PUBLICATIONS

International Search Report for PCT/NL2019/050620 (PCT/ISA/210) dated Feb. 17, 2020.
Written Opinion of the International Searching Authority for PCT/NL2019/050620 (PCT/ISA/237) dated Feb. 17, 2020.

* cited by examiner

MILKING SYSTEM WITH DETECTION SYSTEM

The present invention relates to a milking system, comprising a milking means with a milking control device and arranged for milking milk from a dairy animal, a milk line in fluid connection with the milking device, a sampling and analysis device arranged to take a sample of the milk from the milk line and to analyse milk from the sample, wherein the milking control device is arranged to control the milking based on a result of said analysis, wherein the sampling and analysis device comprises a reagent carrier, comprising a base tape layer to which base type layer there is provided a reagent in the form of a reagent pad that is arranged to provide a detectable response in the presence of at least one substance in the milk from the sample, a dosing device arranged to provide a droplet of said milk from said sample onto the reagent pad, an optical radiation source for emitting optical source radiation onto the reagent pad, and an optical sensor device arranged to detect optical response radiation emitted by the reagent pad in response to said emitted source radiation received by said reagent pad, and to analyse the detected optical response radiation to provide an indication of a presence or concentration of said at least one substance in said droplet.

Such milking systems are in principle known in the art. Milking systems are often provided with such sampling and analysis devices to be able to monitor milk quality. In particular robotic milking systems require such monitoring due to regulations.

A problem with the known milking systems is that the analysis results are not always satisfactory. Sometimes a halo or other artefact is found at the rim of the place where the drop wetted the reagent. Another problem that occurs is that the temporal development of the response in the reagent can not always be followed well enough, which limits the amount of information that can be obtained with the analysis.

An object of the present invention is to provide a milking system of the kind mentioned above in which at least one of these problems has been solved or mitigated.

Thereto, the present invention provides a milking system according to claim 1, in particular a milking system, comprising a milking means with a milking control device and arranged for milking milk from a dairy animal, a milk line in fluid connection with the milking device, a sampling and analysis device arranged to take a sample of the milk from the milk line and to analyse milk from the sample, wherein the milking control device is arranged to control the milking based on a result of said analysis, wherein the sampling and analysis device comprises a reagent carrier, comprising a base tape layer with a first side and an opposite second side, to which first side there is provided a reagent in the form of a reagent pad that is arranged to provide a detectable response in the presence of at least one substance in the milk from the sample, a dosing device arranged to provide a droplet of said milk from said sample onto the reagent pad, an optical radiation source for emitting optical source radiation onto the reagent pad, and an optical sensor device arranged to detect optical response radiation emitted by the reagent pad along an optical path to the optical sensor and in response to said emitted source radiation received by said reagent pad, and to analyse the detected optical response radiation to provide an indication of a presence or concentration of said at least one substance in said droplet, wherein the base tape layer is transmissive to the optical radiation, and wherein the first side faces away from the optical path to the optical sensor device during analysing by the optical sensor device.

It was found by the inventors that looking at the reagent through the tape, the reaction in the reagent was cleaner, and suffered less from the described artefacts such as a halo around the position of the drop on the reagent. Without wishing to be tied to an explanation, it is believed that this may have to do with the inherent inhomogeneity of a drop of fresh milk, for example due to the presence of large and small fat globules. In practice, it is not feasible, or at least very cumbersome, to homogenise the milk sample to such a degree that no such artefacts would occur. But it was also found that these artefacts occur on the surface side only. In addition, or alternatively, artefacts might arise due to the non-zero time that it takes for the milk sample droplet to be absorbed by the reagent. There will often be a surplus of liquid sample for some time. During this time, reagent or at least one or more agents contained in the reagent, may dissolve or at least move into the liquid or onto the surface of the liquid, where they may collect at the rim thereof. Again, this effect does not occur at the other side of the reagent, that faces the base tape layer. In addition to these possible artefacts, it will also be better possible to monitor and follow the temporal development of the reaction in the reagent because that development will not be hindered by any remaining (and opaque) liquid at the surface of the reagent, or by the already present response at that surface, that will almost always only increase in intensity in time. At the reverse surface (underside) of the reagent, such reaction will much less influence the monitoring.

Moreover, having the camera and the reagent with the sample liquid on opposite sides prevents the latter from contaminating the former, since the tape is inbetween. Especially if the camera views from above, gravity additionally assist in preventing this contamination by sample fluid.

In the present invention, the first side faces away from the optical path to the optical sensor device. This is meant to indicate that the sensor device looks through the base tape layer and sees the underside of the reagent, and not the top surface onto which the sample drop is provided. Herein, what counts is the optical path of the radiation coming from the reagent, and not a spatial relationship between the position of the reagent pad and the optical sensor that could be altered by means of e.g. mirrors or other optical devices. One could also say that the optical response radiation emitted by the reagent passes through the base tape layer.

The optical source radiation may comprise visible radiation, i.e. from about 400-780 nm, but also ultraviolet radiation, in particular UV-A radiation, and/or infrared radiation, in particular NIR. The optical response radiation may comprise similar radiation, such as reflected radiation. Herein, the source radiation and the response radiation may differ in spectrum due to absorbance by the reagent or otherwise. It is also possible that the source radiation triggers a reaction in the reagent, that then emits different radiation. A clear example would be fluorescent radiation, that has a longer wavelength than the source radiation. Exceptionally, though not excluded here, the response radiation could be generated solely by the reagent, such as due to a chemical reaction between the droplet of milk and the reagent. In that case the optical radiation source would be superfluous for that particular reaction.

In the present invention, "reagent" means a layer that provides the described response to the presence or concentration of at least one substance in milk. The reagent could e.g. consist of one or more active agents provided as one layer, or one or more active agents in combination with one or more other materials such as a binding agent. It could also comprise an absorbing layer such as a fibrous material, a textile material etc., into which one or more active agents have been supplied. A "reagent pad" means an amount of reagent into which the droplet is able to penetrate once supplied to the reagent. Through capillary action the droplet may spread beyond the contact point. The reagent pad may be one of a series that are separated from each other by a liquid barrier such as the local absence of reagent. Alternatively the reagent could be provided as a single large pad without internal liquid barriers, large enough to receive a plurality of subsequent drops at a mutual distance that is sufficient to not interfere with each other.

The base tape layer is transparent according to the invention. With this is meant that the optical source radiation and the optical response radiation, at least as far as the part used for analysing is concerned, is transmitted for at least 25%, although it will be obvious that a higher percentage is preferred. It is further remarked here that there may be provided additional layers, such as an adhesive layer between the base tape layer and the reagent pad(s), a cover layer, and so on. However, these do not form part of the gist of the invention.

The control of the milking system based on the analysis results may be in-line, wherein the analysis result for the present milking is used to control the present milking. This could relate e.g. to sampling and analysing foremilk. In case there are visible physical changes in the milk, such as blood, pus or flakes, the milk may not be used for human consumption and must be separated. In milking systems, in particular robotic milking systems without human supervision, this check is performed by means of one or more sensors, such as the present sampling and analysis device. The result of analysing foremilk should be available at the latest when milking is completed, which leaves a time of about five to ten minutes. It is also possible to sample and analyse the main milk. Thereto, it is advantageous when a representative milk sample is taken, which means that sampling is performed during the main milking, at various times, to account for variations during said milking. It will be clear that the analysis result should then be available almost in real-time, or the analysis result is used for subsequent milkings.

Particular embodiments and advantages are described in the dependent claims, as well as in the part of the description that follows below.

In embodiments, the base tape layer, during analysing by the optical sensor device, is provided substantially horizontally and wherein the reagent pad faces downward. "Substantially horizontal" is intended to mean that the base tape layer, in its lengthwise direction, makes an angle of at most 45 degrees, with the horizontal, and preferably at most 20 degrees. With such measures, it can efficiently prevented that possible surplus liquid falls off the reagent and onto the sensor device. In addition, it allows to position the sensor device aiming downwardly, which also prevents dust and other dirt from falling onto the sensor device. It also makes a protective window between the sensor device and the reagent superfluous, which helps prevent reflections.

In embodiments, the reagent carrier comprises a tape reel with the base tape layer wound on said tape reel, wherein the reagent is provided on the base tape layer in the form of a series of separate reagent pads, further comprising a tape mover, arranged to move and unwind the tape from the tape reel, in particular the tape mover comprising a collector reel arranged to collect used tape. Although it is possible to provide the reagent pads on separate pieces of base tape layer, such as dry sticks. It is advantageous if the base tape layer has some length, and comprises a, preferably large, series of reagent pads. This allows a prolonged use of the milking system without requiring human intervention, such as to change the tape reel for new reagent pads. Herein, the to-be-used tape is preferably wound onto a reel, or bobbin. After use, i.e. after providing the sample droplet and analysing the reaction, the tape is moved, by means of the tape mover, to provide a further unused reagent pad. Preferably, the tape mover comprises a collector reel arranged to collect used tape, such as in most cassette players. Such tape handling means are well-known and easily implemented, and allow a large design freedom. However, alternative tape movers, such as a simple weight hanging from the tape, are not excluded.

Preferably, the reagent pads are separated by one or more throughgoing laser ablation lines. A tape with reagent pads and such laser ablation lines has been described in the non-prepublished, concurrently filed co-pending US patent application 'Method of producing a reagent tape, reagent tape and milking device with a milk sampling device therewith', application number U.S. 62/735,212. Advantages of such laser ablation lines are that they may be provided very quickly, and may also be also narrow. The former allows the use of a production method in which the reagent is provided on the base tape layer as a continuous layer, which is subsequently "cut up" by means of the laser beam. The latter allows the use of a close spacing between reagent pads, which in turn allows a prolonged use without human intervention, such as to change tape reels. Herein, use is made of the fact, found in practice, that a laser ablation line is an effective barrier for (watery) fluids between neighbouring reagent pads. Note that providing a hydrophobic barrier line on top of a continuous layer of reagent, in order to form separate pads, would work less efficiently, since that requires the hydrophobic material of the barrier line to be provided through the reagent layer down to the base tape layer, not only in order to prevent (capillary) transport of the liquid to a neighbouring pad, but also to be able to see the limits of a reagent pad. This is helpful in positioning the reagent pads correctly in view of the optical sensor. Although for example mechanical positioning means may suffice, it is advantageous to use such optical feedback from the camera.

In embodiments, the dosing device is arranged to provide said droplet to the reagent pad from below the reagent pad. This ensures that during dosing any surplus liquid supplied will, or at least has a chance to, fall off the reagent. This prevents that surplus liquid from causing trouble further down the line, such as near the sensor device. In case the sample drop is provided from below, any surplus liquid will stay on the tape. Note that it is still possible to provide the droplet from above, and then turn the tape around a corner. However, that may cause the surplus liquid from running over the surface of the reagent, possibly towards a neighbouring reagent pad, or falling off the tape in an uncontrolled fashion and position.

In embodiments, the dosing device comprises a nozzle for supplying said droplet, and a cup surrounding the nozzle that is arranged to collect excess liquid from the nozzle during supplying of said droplet, in particular the cup comprising a drain for surplus milk sample fluid. In this way, any surplus liquid will be caught by the cup surrounding the nozzle, and will be prevented from interfering with the reaction, the reagent etc. further down the line. It is also advantageous in that cleaning liquid, such as more milk or water with a cleaning agent, can be provided to the nozzle, the used cleaning liquid then being drained by the drain. Advantageously, there is provided a displaceable countercup, against which the nozzle with the cup is sealingly placeable, together forming a sealed off space for containing liquid ejected by the nozzle. In this way, liquid may even ejected forcefully without entering the environment of the nozzle and cup(s) because the countercup and cup seal off the water from that environment.

In embodiments, the optical sensor device has a first main direction of sensitivity, and wherein the optical radiation source is arranged to emit the optical source radiation in a second main direction onto the second side of the base tape layer, wherein the first direction makes a sharp angle with the second side, the first direction preferably being perpendicular to the second side of the base tape layer. The latter measure ensures that the sensor device has a good view of the reagent pad. The sharp angle ensures that the directly emitted optical source radiation will not be reflected off the base tape layer towards the sensor device, which would cause unwanted glare. As an additional advantageous measure, there could be provided an optical absorber in the centre of the optical radiation source, to decrease the (most) direct radiation, to also prevent glare in the sensor device.

In embodiments, the reagent pad comprises at least two stacked layers of different reagents. In particular, the reagent pad comprises a bottom layer near the tape and stacked thereon a top layer, wherein at least the bottom layer comprises a reagent material configured to provide a detectable response in the presence of at least one substance in the sample, and wherein the top layer causes a first reaction before said detectable response can occur. Such double layers may prove advantageous for various reasons and/or in various circumstances. First, it is possible to have the top layer protect the bottom layer against influences, such as of oxygen, moisture or the like, as long as the top layer is penetratable by the sample liquid, such as dissolvable or the like. This allows much more accurate measurements in the case of particularly sensitive reagent materials. Second, the response may require a two-step reaction with per se incompatible reagent materials, such as a specific acid and a specific base, or the reaction product of the first reaction, in the top layer, is required for another reaction, in the bottom layer, and so on. In such cases, it is desirable to have more time available for observing the response. Furthermore, according to the invention, the camera observes in this case actually the bottom layer. That means that the reaction/response in the top layer does not block, or at least interferes much less with, the reaction in the bottom layer. This is of course best suited if one is interested in observing solely or primarily the reaction in the lowermost layer, such as in the case of flow-through tests (or "vertical" lateral flow tests).

In embodiments, the optical sensor device is arranged such that it sees at least two consecutive reagent pads, as seen in a lengthwise direction along the tape. Herein, it is the number of reagent pads that are completely visible to the sensor device that counts. By having two or more consecutive reagent pads in the field of view of the sensor device, it becomes possible to monitor the response in the reagent pad during a longer period of time. In milking, the time between consecutive starts of milking may be quite short, such as about five minutes. That leaves only a short time for monitoring the response. In turn, this requires a relatively large amount or concentration of active agent(s) in the reagent. These active agents are often enzymes, antibodies or the like, which are quite difficult to produce and therefore require a lot of resources. By now allowing more reagent pads in the field of view, and thus a longer time to monitor, such amount or concentration may be lower, and thus the reagent pad is easier to produce. Herein, it is noted that in particular optical sensor systems very often have such a good resolution that the smaller size of the reagent pad in the view of the sensor device is not very limiting.

Figure 2:
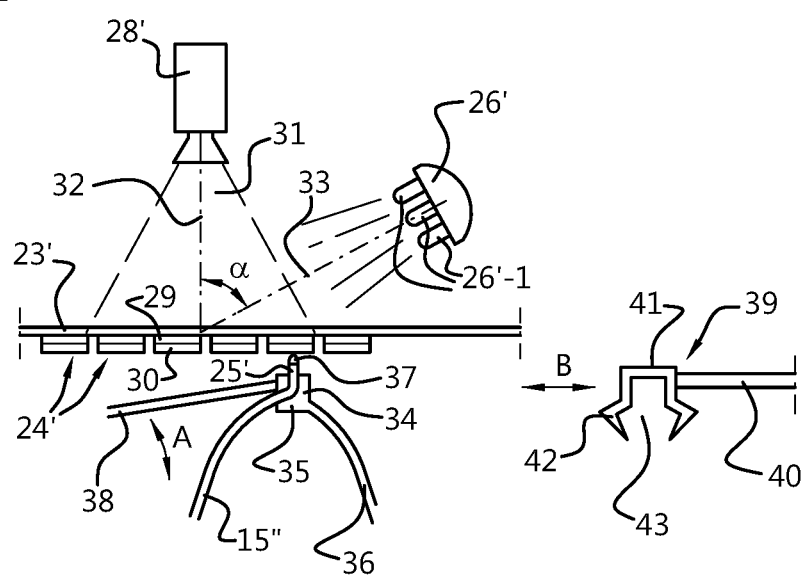

The invention will now be elucidated by way of a number of exemplary embodiments and the drawings, in which FIG. 1 shows a diagrammatic representation of a milking system according to the present invention; and FIG. 2 diagrammatically shows a partly cross-sectional view through a part of an embodiment of the invention.

FIG. 1 shows a diagrammatic representation of a milking system 1 according to the present invention for milking teats 101 of an udder 100 of a dairy animal. The milking system 1 comprises teat cups 2, connected to short milk lines 3, debouching in a milk jar 4, that in turn is connected to a main milk line 5. A milk pump is denoted 6, and a three-way valve with 7 connects to a bulk tank line 8 connected to a bulk milk tank 9, and to a sewer line 10.

A milking robot 11 has a robot arm 12 and a robot control unit 13. A sampling unit is generally denoted 14, and a sampling line 15 with an optional sample valve 16. The sampling unit 14 comprises a supply reel 20 and a collecting reel 21 that is driven by a tape mover 22, for positioning a tape 23 with reagent pads 24. A nozzle device for sample droplets is denoted by 25, a light source 26 emits light 27, and a camera is denoted by 28.

In use of the milking system 1, the robot control unit 13 controls the milking robot 11 with the robot arm 12 to attach the teat cups 2 to the teats 101 of the udder 100 of a dairy animal such as a cow. The milk that is subsequently milked leaves the teat cups 2 under the influence of a vacuum, that is applied by a pump not depicted here, via the short milk lines 3, and is collected in a milk jar 4.

In order to comply with legal requirements, the first milk from each teat must be tested for physical changes, and if desired for other deviant properties. This can be done by means of a separate foremilk test device, or it can be done with the help of the sampling unit 14 as supplied according to the invention. Then use will be made of the alternative sample lines 15'. In case of a negative assessment, the milked milk collected in the milk jar 4 will then be pumped to the sewer line 10 by means of the milk pump 6, via the main milk line 5 and the three way valve 7. All these devices are under the control of the robot control unit 13. Contrarily, if the milk is assessed to be of good quality, it will be pumped to the bulk milk tank 9 via the bulk line 8.

It is also possible that the sampling unit 14 takes a sample from the milk jar 4, in particular a mixed sample from milk that was milked from all teats and during all of the milking. This helps to get a good assessment of the milk that (if not rejected based on the foremilk assessment or otherwise, such as being antibiotics milk) will be sent to the bulk tank 9, or possible to one of several bulk milk tanks. For example, the milk from different cows could be sent to different bulk tanks, based on their fat content, their protein content or otherwise, as determined by the sampling unit 14. In such embodiments, as the one shown in FIG. 1, the sample line 15 runs from the milk jar 4 to the sampling unit 14, and optionally has a sample valve 16. Note that the latter could also be a part internal to the sampling unit 14.

Most often, however, the sampling unit 14 is used to determine a property of the milk from a cow, either per teat quarter 101 or for the whole udder 100/animal, which property is subsequently used in animal management but not for immediate control of the milk destiny. Examples are the measurement of hormones such as progesterone, that play a role in the reproductive cycle of the animal, or of substances that relate to feeding or metabolic health of the animal. Based on the assessment by the sampling unit 14, the farmer or the control unit 13 may then adapt feeding, call a veterinary for a health check or for insemination, and so on. It is remarked that in robotic milking systems animal identification systems are present, so that animal ID during milking is known. Thereby, any measurement result will be coupled to the corresponding animal file in a database system.

Furthermore, a sampling unit 14 is very generally shown here, in that it contains a supply reel 20 and a collecting reel 21, between which a tape 23 is advanced by means of tape mover means 22, such as a cassette deck motor or stepper motor. The tape 23 carries reagent pads 24 that contain reagent that gives a detectable response in the presence of a defined substance, often the intensity of the response depending on the concentration of the substance brought into the reagent via the sample droplet. Such a sample droplet is delivered via the nozzle 25. A light source 26 then shines light 27 onto the reagent pad 24, and a camera 28 observes the response, if any, in the reagent pad. The light source 26 may be any suitable light source, such as one or more LEDs, and the emitted light 27 may be visible light, UV(A) radiation, (near) infrared, and so on, depending on the used reagent. Of course, the camera 28 should be adapted to detect radiation coming from the reagent pad 24. Often, this is reflected or scattered light, but it could be different radiation, such as fluorescence radiation. In any case, details of such radiation and detection may easily be implemented by the skilled person and do not form the present invention as such.

FIG. 2 diagrammatically shows a partly cross-sectional view through a part of an embodiment of the invention. Herein, similar parts are given the same reference numerals, sometimes with a prime (').

Here, the tape 23' is provided with a series of reagent pads 24' that have a bottom layer 29 and a top layer 30. The nozzle 25' is connected to the sample line 15", provides a sample droplet 37, and is provided in, and surrounded by, an overflow cup 34, which has an overflow space 35 with a drain 36 and is connected to a nozzle mover arm 38 that is moveable in the direction of the double arrow A. A rinsing cup 39 is moveable by means of a connected rinsing cup moving arm 40 in the direction of the double arrow B, and comprises a bottom 41 and a bellows 42, and surrounds a rinsing space 43. The camera 28' has a field-of-view 31 with a line of main direction 32. The light source 26' comprises three LEDs 26'-1 and shines in an solid angle with a line of main direction 33, that makes an angle α with line 32.

In use of the system, first the nozzle 25' can rinsed with fluid, to remove residues from previous sampling and/or to bring the nozzle to a desired temperature, by rinsing with correspondingly heated fluid. This may be done by supplying liquid through the sample line 15", and collecting the liquid emerging from the nozzle 25' in the overflow cup 34 by means of gravity. However, it is advantageous if the liquid for rinsing is supplied more vigorously. This can be achieved by moving the nozzle somewhat away from the tape 23', and moving the rinsing cup 39 between the nozzle and the tape, followed by inserting the nozzle into the rinsing space 43. Preferably, the nozzle 25' with the overflow cup 34 are sealed by the bellows 42 of the rinsing cup 39. Thereby, the overflow space 35 and the rinsing space 43 form one sealed off space. Now, rinsing fluid may be supplied to the nozzle 25' with vigour, such as with 2 m/s.

The liquid will then be ejected from the nozzle but remain within the overflow space/rinsing space 35/43. From there, the fluid will be drained by means of the drain 36. Finally, it will be ensured that the nozzle is completely filled with sample liquid, in particular milk, by pressing the nozzle 15" against the bottom 41 of the rinsing cup 39 and eject more liquid. The bottom 41 is somewhat elastic, and this ensures that there will be a clearly defined meniscus of sample liquid in the now completely filled, and air bubble-less nozzle. The nozzle arm 38 will then move the nozzle downward, out of the rinsing cup 39, and the rinsing cup moving arm 40 will move the rinsing cup 39 to the side, to clear the way for the nozzle to reach the reagent pads.

Next, a dosing pump such as a peristaltic pump may dose a known amount of sample fluid, to form the sample droplet 37 of now known dimensions. This helps in preventing excess fluid that may drop off unexpectedly, and also ensures that it will be known when the droplet 37 will touch the reagent pad 24". The nozzle mover 38 will then move upward again to bring the droplet 37 to a reagent pad 24', where a reaction and response may be brought about.

This reaction can be observed by the camera 28', that looks straight down through the tape, with a field-of-view 31 with a central line 32. This allows the camera 28' to observe the reaction in the reagent pad 24' from the opposite side with respect to the sample liquid supplied in the droplet 37. This prevents that already coloured reagent material blocks the observation of further response in fresh reagent material, or that not yet absorbed sample liquid blocks the view altogether. This is particularly helpful in double layer reagent pads such as shown in the figure. Sometimes it takes a two-step reaction, such as in the case of flow-through tests. Herein, the present set-up with the double layer may provide an alternative to these flow-through tests or also lateral flow tests. Since these take more time, it is then advantageous when more than one reagent pad 24' is in the field-of-view 31, since the tape and thus each pad 24' is advanced one pad length for every sampling, such as for every milking. Since the later may be as short as five minutes, it is advantageous to allow more pads in the view of the camera 28' to allow more time for observing the response. It is remarked that even with single layer reagent pads 24', having more pads in view of the camera is useful, since then the concentration of the reagent in the pad 24' may be less than would be needed if the response would have to be assessed in those five minutes.

It is remarked that the camera 28' need not itself be positioned (directly or not) above the tape 23', as long as the optical path (the "view") of the camera 28' is on the other side of the tape 23' as where the reagent pads 24' are. In other words, the camera should look through the tape. The physical position of the camera 28' may be changed e.g. by using mirrors or the like. These may e.g. be used to fold up the optical path, and make the analyser device more compact.

The light source 26' used in the present embodiment comprises three LEDs 26'-1. These can be white light LEDs that together shine a homogeneous but bright light, in a main direction 33 that makes a sharp angle α with the line 32 of the camera's field-of-view, in order to prevent blurring or glaring of the camera image. The light source may also comprise other types, such as a combination of red, green and blue LEDs, halogen incandescent and so on. The light emitted may be visible light, near infrared, ultraviolet (UVA) or the like. The tape 23' should of course be transparent for the light used.

The above described embodiments only serve to help explain the invention without limiting this in any way. The scope of the invention is rather determined by the appended claims.

The invention claimed is:

1. A milking system, comprising:
a milking device with a milking control device and arranged for milking milk from a dairy animal, a milk line in fluid connection with the milking device, and a sampling and analysis device arranged to take a sample of the milk from the milk line and to analyse milk from the sample,
wherein the milking control device is arranged to control the milking based on a result of said analysis,
wherein the sampling and analysis device comprises:
a reagent carrier, comprising a base tape layer with a first side and an opposite second side, to which first side there is provided a reagent in the form of a reagent pad that is arranged to provide a detectable response in the presence of at least one substance in the milk from the sample;
a dosing device arranged to provide a droplet of said milk from said sample onto the reagent pad;
an optical radiation source for emitting optical source radiation onto the reagent pad; and
an optical sensor device arranged to detect optical response radiation emitted by the reagent pad along an optical path to the optical sensor and in response to said emitted source radiation received by said reagent pad, and to analyse the detected optical response radiation to provide an indication of a presence or concentration of said at least one substance in said droplet, and
wherein the base tape layer is transmissive to the optical radiation, and wherein the first side faces away from the optical path to the optical sensor device during analysing by the optical sensor device,
wherein the dosing device is arranged to provide said droplet to the reagent pad from below the reagent pad.

2. The milking system according to claim 1, wherein the base tape layer, during analysing by the optical sensor device, is provided substantially horizontally and wherein the reagent pad faces downward.

3. The milking system according to claim 1, wherein the reagent carrier comprises a tape reel with the base tape layer wound on said tape reel, wherein the reagent is provided on the base tape layer in the form of a series of separate reagent pads,
further comprising a tape mover, arranged to move and unwind the tape from the tape reel.

4. The milking system according to claim 1, wherein the reagent pads are separated by one or more throughgoing laser ablation lines.

5. The milking system according to claim 1, wherein the dosing device comprises a nozzle for supplying said droplet, and a cup surrounding the nozzle that is arranged to collect excess liquid from the nozzle during supplying of said droplet.

6. The milking system according to claim 1, wherein the optical sensor device has a first main direction of sensitivity, and wherein the optical radiation source is arranged to emit the optical source radiation in a second main direction onto the second side of the base tape layer, wherein the first direction makes a sharp angle with the second side.

7. The milking system according to claim 1, wherein the reagent pad comprises at least two stacked layers of different reagents.

8. The milking system according to claim 1, wherein said optical sensor device is arranged such that the optical sensor sees at least two consecutive reagent pads, as seen in a lengthwise direction along the tape.

9. The milking system according to claim 1, wherein the reagent carrier comprises a tape reel with the base tape layer wound on said tape reel, wherein the reagent is provided on the base tape layer in the form of a series of separate reagent pads,
further comprising a tape mover, arranged to move and unwind the tape from the tape reel, the tape mover comprising a collector reel arranged to collect used tape.

10. The milking system according to claim 1, wherein the dosing device comprises a nozzle for supplying said droplet, and a cup surrounding the nozzle that is arranged to collect excess liquid from the nozzle during supplying of said droplet, the cup comprising a drain for surplus milk sample fluid.

11. The milking system according to claim 1, wherein the optical sensor device has a first main direction of sensitivity, and wherein the optical radiation source is arranged to emit the optical source radiation in a second main direction onto the second side of the base tape layer, wherein the first direction makes a sharp angle with the second side, the first direction being perpendicular to the second side of the base tape layer.

12. The milking system according to claim 2, wherein the reagent carrier comprises a tape reel with the base tape layer wound on said tape reel, wherein the reagent is provided on the base tape layer in the form of a series of separate reagent pads,
further comprising a tape mover, arranged to move and unwind the tape from the tape reel.

13. The milking system according to claim 2, wherein the reagent pads are separated by one or more throughgoing laser ablation lines.

14. The milking system according to claim 3, wherein the reagent pads are separated by one or more throughgoing laser ablation lines.

15. The milking system according to claim 2, wherein the optical sensor device has a first main direction of sensitivity, and wherein the optical radiation source is arranged to emit the optical source radiation in a second main direction onto the second side of the base tape layer, wherein the first direction makes a sharp angle with the second side.

16. The milking system according to claim 3, wherein the optical sensor device has a first main direction of sensitivity, and wherein the optical radiation source is arranged to emit the optical source radiation in a second main direction onto the second side of the base tape layer, wherein the first direction makes a sharp angle with the second side.

* * * * *